United States Patent
Deleuran

(12) 
(10) Patent No.: US 6,255,299 B1
(45) Date of Patent: Jul. 3, 2001

(54) OPTHALMIC GEL COMPOSITION AND METHOD OF TREATING EYE INFECTIONS

(75) Inventor: Merete Deleuran, Allerød (DK)

(73) Assignee: Leo Pharmaceutical Products Ltd., Ballerup (DK)

( * ) Notice: Subject to any disclaimer, the term of this patent is extended or adjusted under 35 U.S.C. 154(b) by 0 days.

(21) Appl. No.: 08/092,574

(22) Filed: Jul. 16, 1993

Related U.S. Application Data

(62) Continuation of application No. 07/794,707, filed on Nov. 20, 1991, now abandoned, which is a continuation of application No. 06/908,802, filed as application No. PCT/DK86/00002 on Jan. 7, 1986, now abandoned.

(30) Foreign Application Priority Data

Jan. 7, 1985 (DK) .................................................. 8500310

(51) Int. Cl.$^7$ .................................................. A61K 31/56
(52) U.S. Cl. .......................................... 514/182; 514/912
(58) Field of Search ...................................... 514/182, 912

(56) References Cited

U.S. PATENT DOCUMENTS

| | | | |
|---|---|---|---|
| 3,072,531 | * 1/1963 | Godtfredsen et al. | 514/182 |
| 3,334,014 | * 8/1967 | Godtfredsen et al. | 514/182 |
| 4,100,276 | * 7/1978 | von Daehne et al. | 514/182 |
| 4,271,143 | * 6/1981 | Schoenwald et al. | 514/397 |
| 4,407,792 | 10/1983 | Schoenwald et al. | 414/81 |
| 4,795,436 | 1/1989 | Robinson | 424/422 |
| 4,983,392 | 1/1991 | Robinson | 424/427 |

FOREIGN PATENT DOCUMENTS

| | | | |
|---|---|---|---|
| 2654508 | 6/1977 | (DE) | A61K/31/575 |
| 2654508 | 7/1977 | (DE) | A61K/31/575 |
| 135267 | 3/1977 | (DK) | A61K/9/06 |
| B 135267 | 3/1977 | (DK) | A61K/9/06 |
| 0020794 | 1/1981 | (EP) | A61K/9/10 |
| 2407714 | 6/1979 | (FR) | A61K/9/00 |
| 2007091 | * 5/1979 | (GB) | . |
| 2013084 | 8/1979 | (GB) | A61K/9/10 |
| 8502092 | 5/1985 | (WO) | A01N/25/26 |

OTHER PUBLICATIONS

Chem. Abst. 104: 199554(c) (1986)–Hansen.*
Hansen, S. "Intraocular penetration of fusidic acid with topical Fucithalmic ®," European Journal of Drug Metabolism and Pharmaco–kinetics, 1985, vol. 10, No. 4, pp. 329–31.*
Medline abstract AN 86164451 of Hansen.*
*Remington's Pharmaceutical Sciences*, 1975, pp. 1537–38.
*Rote Liste 1977/78*.
Chadwick et al, *Brit. J. Ophthal.*, 53(1):26–29 (1968).
Schoenwald et al, *J. Phar. Sc.*, 67(9):1280–83 (1978).
Graf et al, *Acta Pharm. Tech.*, 29(3):209–15 (1983).
Saettone et al, *Comm. J. Pharm. Pharmacol.*, 32:519–521 (1980).
Bottari et al, *Can. J. Pharm. Sci.*, 14(2):39–43 (1979).
ABD–Elbary et al, *Pharmazie*, 36:356–358 (1981).
Baun et al, *Pharm. Acta Helv.*, 46:94–113 (1971).
International Publication No. WO84/04080 (Dec. 6, 1984).
International Publication No. WO84/04681 (Dec. 6, 1984).
Remington's Pharmaceutical Sciences, 1975, pp. 1537–38.
Rote Liste 1977/78.
Chadwick et al, Brit. J. Ophtal., 53(1):26–29 (1968).
Schoenwald et al, J. Phar. Sc., 67(9):1280–83 (19778).
Graf et al, Acta Pharm. Tech., 29(3):209–15 (1983).
Saettone et al, Comm. J. Pharm. Pharmacol., 32:519–521 (1980).
Chemical Abstract 104:199554(c) (1986) (Hansan).
Bottari et al, Can. J. Pharm. Sci., 14(2):39–43 (1979).
ABD–Elbary et al, Pharmazie, 36:356–358 (1981).
Baun et al, Pharm. Acta Helv., 46:94–113 (1971).
International Publication No. WO 84/04080 (Dec. 6, 1984).
International Publication No. WO 84/04681 (Dec. 6, 1984).

* cited by examiner

*Primary Examiner*—Zohreh Fay
(74) *Attorney, Agent, or Firm*—Pillsbury Winthrop LLP

(57) ABSTRACT

An ophthalmic gel composition for human and veterinary use comprising 0.5–4% w/v of fusidic acid suspended in an aqueous vehicle containing 0.2–2% w/v of a polyanionic polymer.

4 Claims, No Drawings

OPTHALMIC GEL COMPOSITION AND METHOD OF TREATING EYE INFECTIONS

This is a continuation of Application No. 07/794,707, filed on Nov. 20, 1991, which was abandoned upon the filing hereof which is a continuation of Ser. No. 06/908,802, filed Sep. 4, 1986, now abandoned, which is a 371 of PCT/DK86/00002, filed Jan. 7, 1986.

The present invention relates to an ophthalmic gel composition for human and veterinary use comprising an ophthalmic drug and a vehicle based on a polyanionic polymer.

One of the major problems of topical ophthalmic therapy is to maintain an adequate concentration of the ophthalmic drug at the desired site of action for a prolonged period of time. Thus, only a small volume of preparation can be contained in the fornix inferior and the preparation applied tends to be diluted by the tears and to be drained through the nasolacrimal duct.

It is well known that the duration of action of cationic ophthalmic drugs may be increased by incorporating such drugs into gels based on polyanionic polymers, cf. DE-OS 29 02 863, R. D. Schoenwald et al: Influence of high-viscosity vehicles on miotic effect of pilocarpine, Jour. of Pharm. Sciences, Vol. 67, No. 9, September 1978, 1280–1283, F. Bottari et al: Semisolid ophthalmic vehicles II: Evaluation in albino rabbits of aqueous gel-type vehicles containing lidocaine and benzocaine, Can. J. of Pharm. Sci., vol. 14, No. 2 1979, 39–43, and Engelbert Graf et al: Interaction of Carbopol® 934, with diphenhydramine and dexchlorpheniramine, Acta Pharmaceutica Technologica, 29 (3), 1983, 209–215.

These gel compositions exhibit a duration of action which is about twice that of a conventional ophthalmic drug preparation.

Surprisingly, it has now been found that eye infections can be combatted very effectively with a composition comprising fusidic acid suspended in a gel of the above mentioned type.

The composition of the invention comprises from 0.1 to 4% w/v of fusidic acid suspended in an aqueous vehicle containing from 0.2 to 2% w/v of polyanionic polymer.

The surprising efficiency of the composition of the invention is evidenced by the fact that the duration of action is about 10 times that of a preparation based on fusidic acid and a conventional gelling agent, cf. the example below.

The very substantial prolongment of the action of fusidic acid is particularly surprising, since hitherto it was believed that the prolonged action of the prior art compositions is based on an interaction of a positively charged drug with the negatively charged polymer. Thus, it might be expected that a drug, such as fusidic acid, which is negatively charged at the pH value of the eye, i.e. about 7.4, would be unable to interact with the polyanionic polymer and to provide a prolonged action.

The composition of the invention is particularly useful for the local treatment of eye infections. Thus, whereas conventional ophthalmic preparations, such as chloroamphenicol eye drops, have to be applied 5–6 times daily or even more, it is sufficient to apply preparations based on the composition of the invention 1–2 times daily.

The composition of the invention preferably contains about 1% w/v of fusidic acid in the form of particles having a particle size not exceeding 10 μm and preferably between 2 and 5 μm.

A polyanionic polymer is preferably a carboxyvinyl polymer having a molecular weight of from about 400.000 to about 6 million. The viscous solutions which are formed during the preparation of the ophthalmic polymer suspension have a viscosity of from 10 to about 20.000 cps at 25° C. measured on a RVT Brookfield Viscosimeter.

The polyanionic polymer is preferably of the type which is commercially available under the trade name "Carbopol" (B.F. Goodrich Company). A particularly preferred polyanionic polymer is "Carbopol 934". The "Carbopol" polymers do not blur the normal vision because the gel structure breaks down shortly after application to the eye under the influence of ions contained in the lacrimal fluid.

The pH value of the composition of the invention is preferably from 5.0 to 6.5 and more preferably about 5.8.

The adjustment of the pH value is preferably effected with a pharmaceutically and physiologically acceptable base, such as sodium hydroxide.

A preparation based on the composition of the invention may contain auxiliary agents, such as preservatives, stabilizing agents and bacteriostatic agents.

Preparations based on the composition of the invention are preferably used in dosages of from 5 to 100 mg and more preferably from 20 to 50 mg when the preparation is applied into the fornix inferior of an infected eye.

The frequency of dosing varies dependant upon the severity of the infection. However, as mentioned above an application twice a day ordinarily suffices.

The invention also relates to a method of treating eye infections, said method comprising applying an effective amount of a preparation based on the composition of the invention into the fornix inferior of the infected eye.

The invention will be described in detail with reference to the following non-limiting example:

EXAMPLE

An eye preparation having the following composition per ml was prepared:

Preparation A:

| | |
|---|---|
| Fusidic acid, micronized, sterile | 10 mg |
| "Carbopol 934" | 5 mg |
| Sodium hydroxide, 5 N, q.s. for pH 5–6.0 | |
| Mannitol | 50 mg |
| Benzalkonium chloride | 0.1 mg |
| Tetracemin disodium | 0.5 mg |
| Water, sterile, to make | 1 ml. |

Benzalkonium chloride, tetracemin disodium and mannitol are dissolved in sterile water.

The "Carbopol 934" is suspended aseptically in the solution and sterilized by autoclaving at 120° C. for 20 minutes. The suspension is cooled and the sterile fusidic acid is suspended therein. Finally, the suspension is neutralized by addition of sterile sodium hydroxide solution.

The preparation (in the following called Preparation A) thus prepared was compared with a preparation of fusidic acid suspended in a vehicle based on a conventional gel forming agent and further containing preservatives, tonicity agents and a buffer. This preparation (in the following called Preparation B) had the following composition per ml:

Preparation B:

| | |
|---|---|
| Fusidic acid, micronized, sterile | 10 mg |
| Hydroxyethylcellulose | 4 mg |

| | | |
|---|---|---|
| Methyl cellulose | 0.2 mg | |
| Sodium acetate | 1 mg | |
| Glacial acetic acid, q.s. for pH 5–6.0 | | |
| Sodium chloride | 9 mg | |
| Phenethanol | 2.5 mg | |
| Water, sterile, to make | 1 ml. | |

The two preparations were compared in the following manner:

Five New Zealand white rabbits weighing about 3 kg were used in the studies. They were designated Nos. 1–5 and placed in restraining boxes during the first 6 hours of the investigation period and at the 24 hour sampling. Between the 6 hour and the 24 hour sampling, the animals were housed individually and given pelleted food and water ad libitum.

Samples for microbiologic determination were taken by placing 6.0 mm AA discs (Whatman) in the fornix inferior, closing the eye lids for approximately 10 seconds and removing the discs with forceps. The discs were placed on the surface of inoculated agar dishes, 14 cm in diameter, together with discs which has been pre-treated with standard solutions for 10 seconds.

The petri dishes were incubated for 16–18 hours at the optimum temperature for the test organisms in question. The inhibition zones of the samples were measured and interpolated on the standard curve which was established as the best response line from the inhibition zones for the standard solutions.

Prior to each investigation the lacrimal fluid of each rabbit was tested for the absence of substances which are inhibitory to the test organisms.

One drop of each preparation was instilled in the fornix inferior of the left eye of each of the five rabbits. Samples were taken at 1, 2, 4, 6 and 24 hours following treatment.

There was a period of at least 72 hours between treatments with different preparations.

The results are presented in the table which shows that fusidic acid is present in measurable concentrations 24 hours after the treatment.

However, the concentration of fusidic acid in the 24 hour samples is approximately ten times higher for preparation A than for preparation B.

TABLE

| | Animal | mcg fusidic acid per ml lacrimal fluid Hours after treatment | | | | | |
|---|---|---|---|---|---|---|---|
| | No. | 0 | 1 | 2 | 4 | 6 | 24 |
| Preparation A | 1 | — | 45 | 45 | 25 | 20 | 6 |
| | 2 | — | 32 | 20 | 6 | 5 | 4 |
| | 3 | — | 113 | 24 | 20 | 4 | 5 |
| | 4 | — | 32 | 28 | 40 | 22 | 4 |
| | 5 | — | 57 | 18 | 6 | 15 | 4 |
| Preparation B | 1 | — | 14 | 5 | 5 | 3 | 0.4 |
| | 2 | — | 20 | 12 | 11 | 8 | 0.2 |
| | 3 | — | 28 | 28 | 8 | 6 | 0.6 |
| | 4 | — | 23 | 10 | 4 | 4 | 0.4 |
| | 5 | — | 34 | 12 | 10 | 4 | 0.5 |

—: indicates a value lower than the detection limit of 0.02 mcg fusidic acid per ml.

What is claimed is:

1. A method of treating eye infections comprising applying an effective amount of an ophthalmic gel composition comprising about 1% w/v of fusidic acid in the form of particles having a particle size of between 2 and 5 μm suspended in an aqueous vehicle containing from 0.2 to 2% w/v of carboxyvinyl polymer, said composition having a viscosity of from 10 to about 20,000 cps at 25° C. measured on a RVT Brookfield Viscosimeter and a pH of from 5.0 to 6.5, said composition being applied as an eye drop into the fornix inferior of the infected eye one or two times daily.

2. A method according to claim 1, said composition comprising

| | | |
|---|---|---|
| Fusidic acid | about 1% | w/v |
| Carboxyvinyl polymer | about 0.5% | w/v |
| Mannitol | about 5% | w/v |
| Benzalkonium | about 0.01% | w/v |
| Tetracemin disodium | about 0.05% | w/v, | said composition also having a pH value of approximately 5.8.

3. A method according to claim 1, wherein the composition is used in dosages of from 5 to 100 mg.

4. A method according to claim 3, wherein the composition is used in dosages of from 20 to 50 mg.

\* \* \* \* \*